United States Patent [19]
Berg et al.

[11] Patent Number: 5,313,048
[45] Date of Patent: May 17, 1994

[54] HIGH TEMPERATURE RESEARCH FURNACE WITH V-SHAPED GUIDE MEMBER

[75] Inventors: Morris Berg; Patrick T. McGuire, both of Champaign, Ill.

[73] Assignee: Morris Berg, Champaign, Ill.

[21] Appl. No.: 909,916

[22] Filed: Jul. 7, 1992

[51] Int. Cl.⁵ .................. G01N 25/02; F27B 5/00
[52] U.S. Cl. ................... 219/390; 219/385; 432/241; 414/154
[58] Field of Search ............ 219/390, 385, 521; 373/115, 109, 137; 432/241, 239, 243, 121; 414/153, 154, 147, 160, 161, 172; 422/63, 65, 67; 118/50.1, 724; 392/418

[56]         References Cited
        U.S. PATENT DOCUMENTS

| 2,966,537 | 12/1960 | Witucki et al. | 219/390 |
| 3,836,325 | 9/1974 | Nakamura et al. | 432/241 |
| 3,860,738 | 1/1975 | Hintenberger | 219/390 |
| 4,417,346 | 11/1983 | Giler | 373/137 |
| 4,462,963 | 7/1984 | O'Brien et al. | 373/130 |
| 4,610,628 | 9/1986 | Mizushina | 432/241 |
| 4,738,618 | 4/1988 | Massey et al. | 432/241 |
| 4,828,490 | 5/1989 | Indig | 432/241 |
| 4,938,691 | 7/1990 | Ohkase et al. | 432/239 |
| 4,976,613 | 12/1990 | Watanabe | 432/241 |
| 5,131,842 | 7/1992 | Miyazaki et al. | 432/241 |

FOREIGN PATENT DOCUMENTS 866392 9/1981 U.S.S.R. .................. 432/239

OTHER PUBLICATIONS

Brochure: Deltech, Inc., "Glass Melting Furnaces" (Publication Data Unknown).
Brochure: CM Furnaces, Inc., "CM Furnaces", 1600, 1700, 1800 Series (Publication Date Unknown).
Article: "Vertical Thermal Processing: Wave of the Future?", Microelectronic Manufacturing and Testing, p. 66, Apr. 1985.
Article: "Design of Low-Mass Furnaces for High Temperatures", Ceramic Bulletin, vol. 67, No. 7, pp. 1186-1187, Nov., 1988.
Article: "Electrically Heated High-Temperature Furnaces", Interceram, vol. 40, No. 3, pp. 143-148 (1991).
Brochure: "Industrial V-Guide Wheels and Track", Bishop-Wisecarver Corp. (1981).
Brochure: "Fiberfrax 970 Paper" and "Fiberfrax Duraboard 2600", Sohio Carborundum, Fibers Division, 6 pages (Feb., 1986).
Brochure: "Refractory Sheet Ceramic Fiber Reinforced Alumina Composites", Sohio Carborundum, Fibers Division, 2 pages (Feb., 1986).
Brochure: "Dayton Linear Actuator, Models 4Z845 and 4Z846", Dayton Electric Mfg. Co. (Publication Date Unknown).

Primary Examiner—Bruce A. Reynolds
Assistant Examiner—John A. Jeffery
Attorney, Agent, or Firm—Willian Brinks Hofer Gilson & Lione

[57]            ABSTRACT

A high temperature bottom-loading research furnace is provided having a lifting mechanism comprising a V-shaped wheels and corresponding guide members for raising and lowering the furnace oven door. The lifting mechanism facilitates precise opening and closing of the door which, along with other mechanical features, reduces the heat loss from the furnace and, accordingly, reduces the amount of energy needed to operate the furnace.

19 Claims, 6 Drawing Sheets

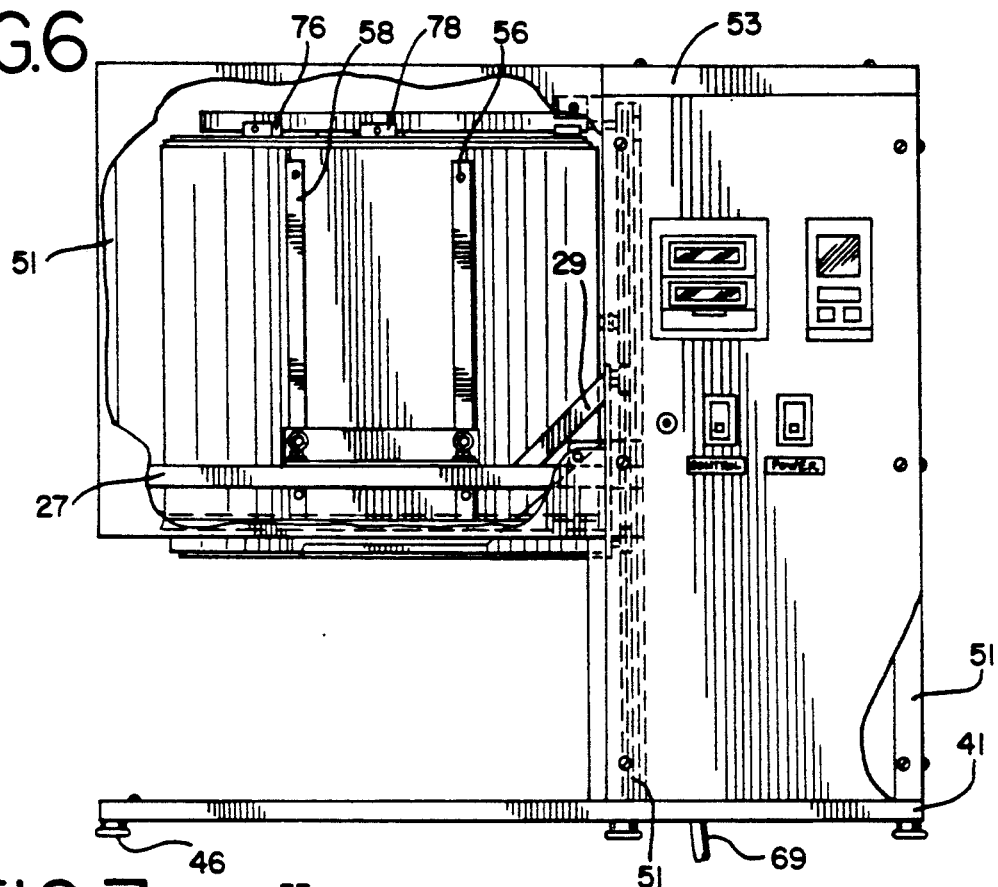
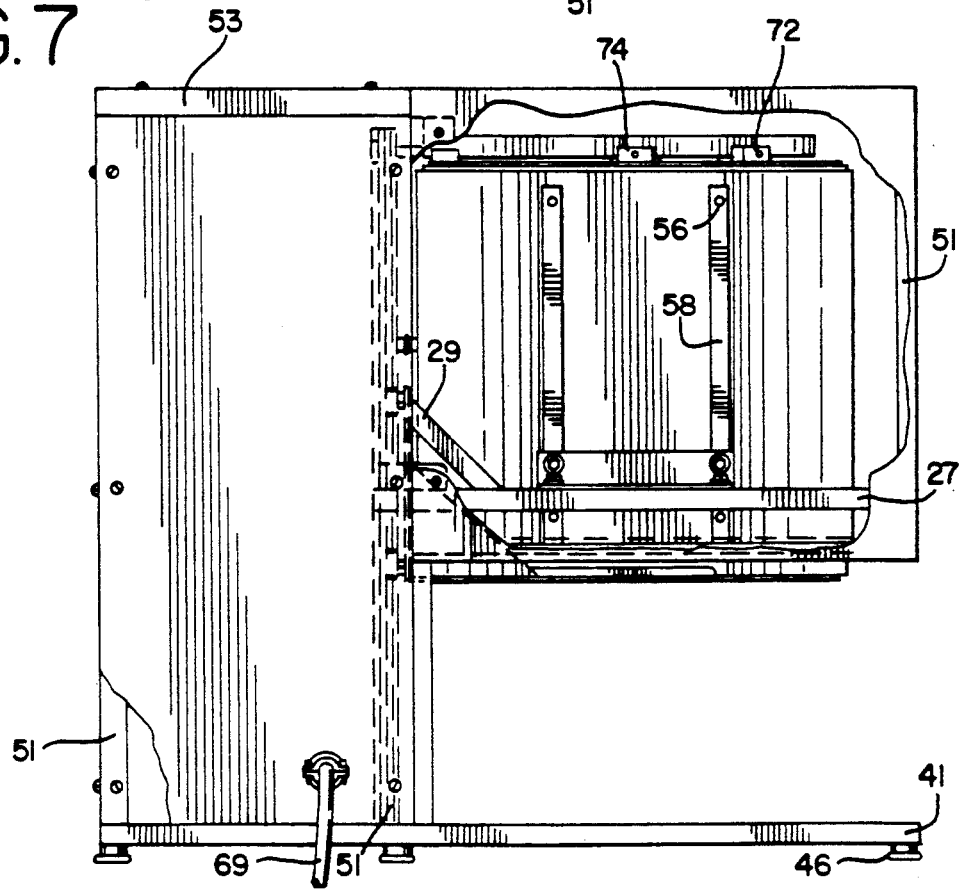

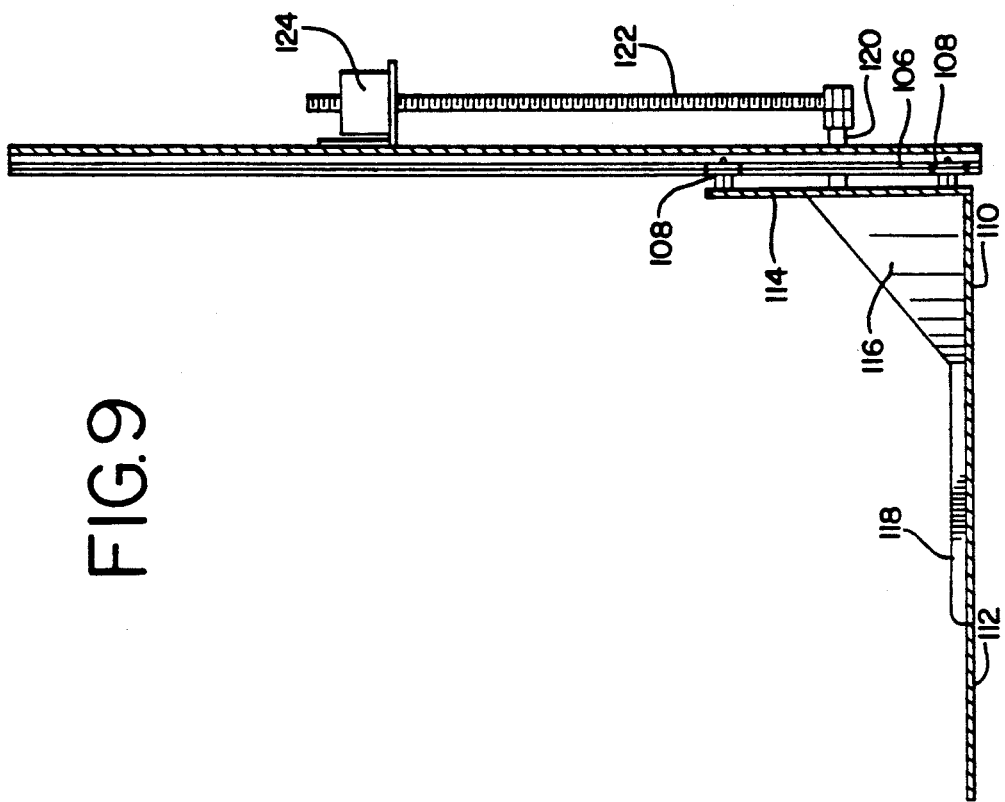
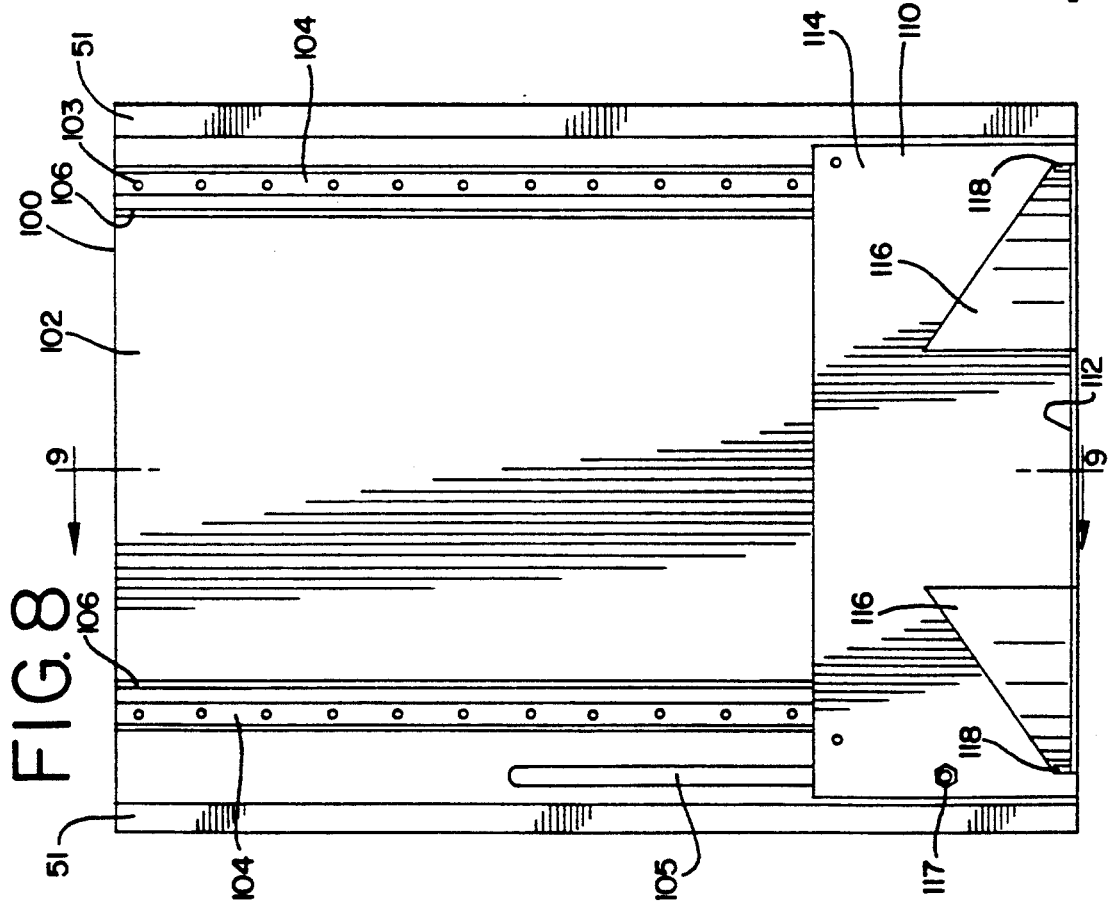

HIGH TEMPERATURE RESEARCH FURNACE WITH V-SHAPED GUIDE MEMBER

FIELD OF THE INVENTION

The present invention is a laboratory scale high temperature research furnace which, due to the presence of an improved lifting mechanism and superior heat containment features, can be brought to and maintained at a high temperature using less energy and power than other research furnaces having similar performance requirements.

BACKGROUND OF THE INVENTION

Electrically powered furnaces which are suitable for use in research laboratories have become popular for a wide variety of research and development applications. Often, these laboratory furnaces are required to reach very high temperatures in order to be useful for various ceramic and metallurgical applications such as crystal growth and sintering of metal and ceramic materials. While the exact furnace requirements vary widely with the specific application, there has been a general demand for furnaces which 1) are relatively lightweight and portable, 2) possess the maximum interior oven space relative to the furnace size, 3) are safe and easy to operate, and 4) require a minimum amount of power and energy for operation. At the same time, it is desirable that the furnaces have the capability of operating at temperatures of 1700° C. or higher, and of reaching such temperatures within a minimal period of time.

The ability of research furnaces to reach very high temperatures within a minimal time period, and to maintain these temperatures using a minimum of energy and power, depends upon several factors including the size and shape of the furnace, the size and position of the door, how well the door fits, the amount of variation or "free play" in the position of the door, the type and amount of insulating material used in the furnace, and other design features which minimize the escape of heat during operation. Initially, many research furnaces used doors which opened in the front of the furnace, and significant efforts and innovations were directed toward minimizing the escape of heat from around the edges of the door. However, it has been known for some time now that furnaces which are loaded from the bottom, through a door opening in the bottom, are advantageous for heat retention due to the tendency of heat to rise.

Nevertheless, heat losses through the doors of bottom loading furnaces can still present a problem where the desired temperatures of the furnaces are high and the differences between the furnaces temperatures and the temperatures of the surrounding environment are large. Typically, a bottom loading furnace is mounted in an elevated position above a stand or platform. A mechanism is provided for opening the door to the furnace by lowering it to the platform, and for closing the door by lifting it to its position in the bottom of the furnace. This type of mechanism is generally known, and will be referred to hereinafter, as a "lifting mechanism".

The lifting mechanism should serve several purposes including lowering the door in a smooth, vibration-free fashion; raising the door into the same exact position every time; and maintaining the door in a tight fitting position, free of movement and play, during operation of the furnace. Due to the importance of the lifting mechanism in minimizing heat loss, much effort has been directed to developing lifting mechanisms which serve one or more of the foregoing objectives. To date, however, inefficiencies have remained in the operation of high temperature bottom loading research furnaces which have resulted in the use of larger than desired heating elements, larger than desired furnace sizes and weights, and larger than desired power and energy requirements.

SUMMARY OF THE INVENTION

The present invention is directed to an improved high temperature research furnace of the bottom loading type. The high temperature research furnace of the invention utilizes a new and improved lifting mechanism which operates in a smooth, vibration-free fashion when raising and lowering the door and which maintains the door in a tight fitting position, free of movement or play, during operation of the furnace. The mechanical structure of the lifting mechanism facilitates precise operation such that the door is made to close in the same tight fitting position every time it is raised by the lifting mechanism, thereby reducing the heat loss around the door to a minimum during operation of the furnace.

The presently preferred embodiment of the invention also embraces a variety of mechanical features, described below, which minimize the heat loss from other parts of the high temperature research furnace. The combination of features, including the new and improved lifting mechanism as well as the other mechanical features described below, result in a highly efficient, portable research furnace which can reach a maximum temperature of 1700° C. or higher, in a relatively short period of time, while being powered only by a standard 115-volt wall circuit. In the past, due to heat losses and other inefficiencies, laboratory research furnaces capable of reaching 1700° C. or higher have required the use of a 230-volt power source in order to operate effectively.

With the foregoing in mind, it is a feature and advantage of the invention to provide a high temperature research furnace for use in laboratories, which operates using an improved lifting mechanism including V-shaped wheels and corresponding guide members to facilitate a uniform, tight fit when closing the furnace door.

It is also a feature and advantage of the invention to provide a high temperature research furnace for laboratory use which is highly efficient and which can operate using a standard 115-volt wall outlet.

It is also a feature and advantage of the invention to provide a high temperature research furnace for laboratory use which is relatively light weight, portable and easy to move from one location to another.

The foregoing and other features and advantages of the invention will become further apparent from the following detailed description of the presently preferred embodiments, when read in conjunction with the accompanying figures and example. It is understood that the detailed description, figures and example are to be construed as illustrative rather than limitative, with the scope of the invention being defined by the appended claims and equivalents thereof.

BRIEF DESCRIPTION OF THE FIGURES

FIG. 6 is a right side cutout view (control panel side) of the furnace with the right protective panel partially removed from the furnace.

FIG. 7 is a left side cutout view of the furnace with the left protective panel partially removed from the furnace.

FIG. 8 is a front view of the lifting mechanism, taken along the line 8—8 in FIG. 1.

FIG. 9 is a right side sectional view of the lifting mechanism of FIG. 8, taken along the line 9—9 in FIG. 8.

DETAILED DESCRIPTION OF THE PRESENTLY PREFERRED EMBODIMENTS

Figure 1:
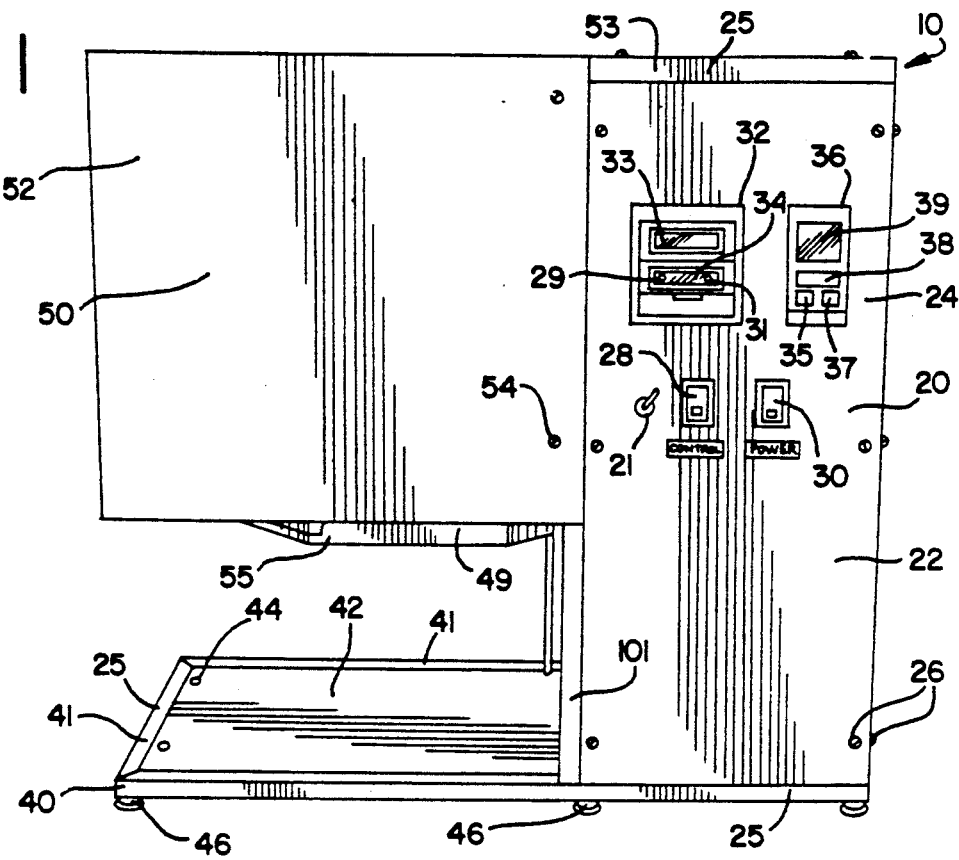
FIG. 1 is a side perspective view of the high temperature research furnace of the invention which illustrates the control panel and the furnace door in the closed position.
Figure 2:
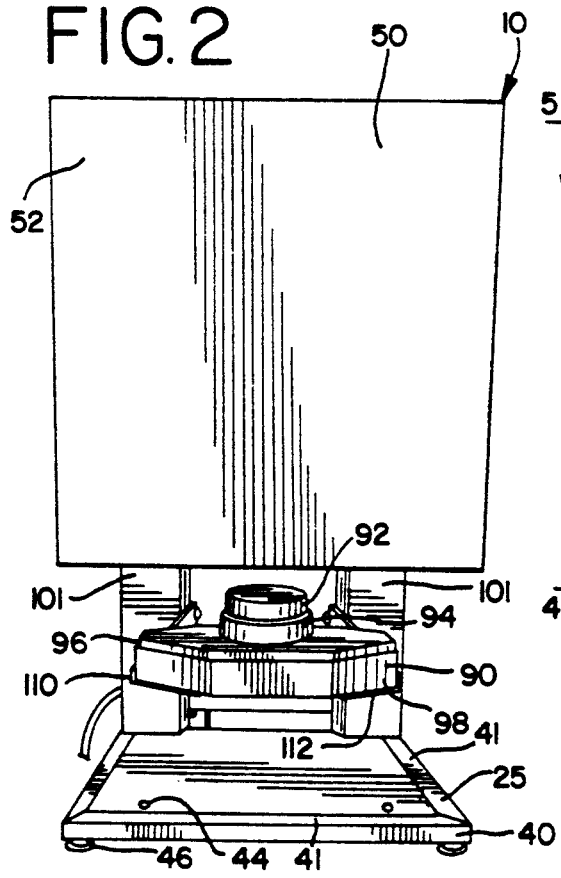
FIG. 2 is a frontal perspective view of the high temperature research furnace of the invention which illustrates the furnace door in the partially open position.
Figure 3:
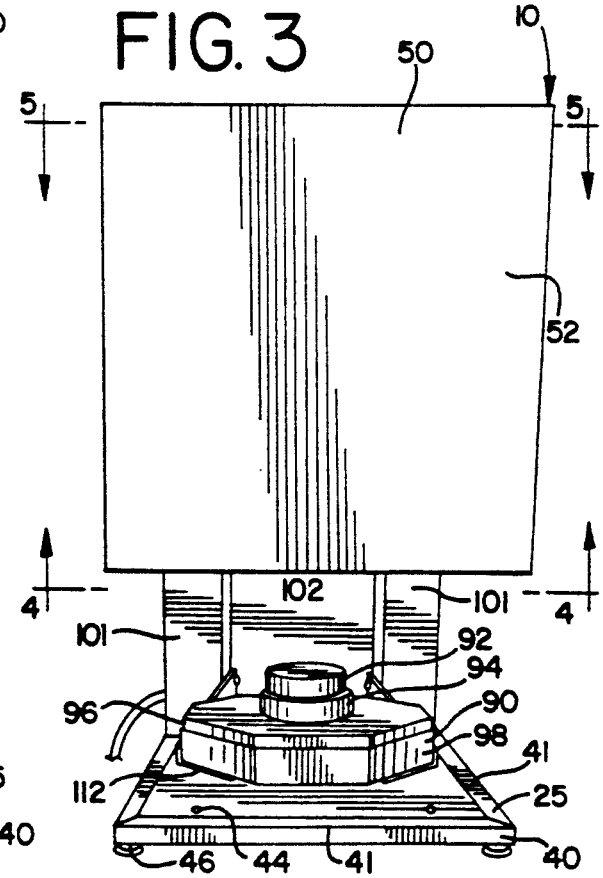
FIG. 3 is a frontal perspective view of the high temperature research furnace of the invention which illustrates the furnace door in the fully open position.

Referring to FIGS. 1-3, a high temperature research furnace 10 of the invention is shown which includes a control cabinet 20, a platform 40 underneath the control cabinet 20, with a portion of the platform extending beyond the control cabinet 20, and an elevated furnace oven 50 located above the portion of the platform 40 which extends beyond the control cabinet 20. The control cabinet 20 is surrounded by protective panels 22 on the top and sides, including a main control panel 24. Preferable, the protective panels 22 are constructed using one-eight-inch thick aluminum plates which are mounted to a stainless steel frame 25 using a plurality of fastener screws 26.

The control panel 24 includes a control switch 28 for activating the power to the control panel 24, and a power switch 30 for activating the power to the furnace oven 50. Above the switches and to the left is located a display instrument 32 having upper and lower display windows 33 and 34. The lower display window 34 includes an indicator light 29 which is activated when the control power switch 28 is "on," and an indicator light 31 which is activated when the oven power switch 30 is "on." The upper display window 33 indicates the amperes of current which are being drawn by the furnace oven 50. An up-down switch 21 is located to the left of the control switch 28, for raising and lowering the oven door 90 using the lifting mechanism 100 described herein.

Located to the right of the display instrument 32 is a program/control instrument 36 which includes setpoint switches 35 and 37, a rate switch 38, a display window 39 and an internal microprocessor (not shown). The setpoint switch 35 is a "touch" control which, when pressed, lowers the temperature setting for the furnace oven 50. The setpoint switch 37 is a touch control which, when pressed, raises the temperature setting for the furnace over 50.

The rate switch 38 is a touch control which can be used to program the rate of heating and cooling of the furnace oven 50. For instance, the rate control 38 can be used to program "ramps" into the temperature control such that, when heated, the furnace temperature rises by a predetermined amount, then holds for a predetermined time period, then rises again by a predetermined amount, then holds again, etc. The display window 39 indicates the temperature setting and the ramping, if any, that has been programmed using the rate control 38.

Figure 4:
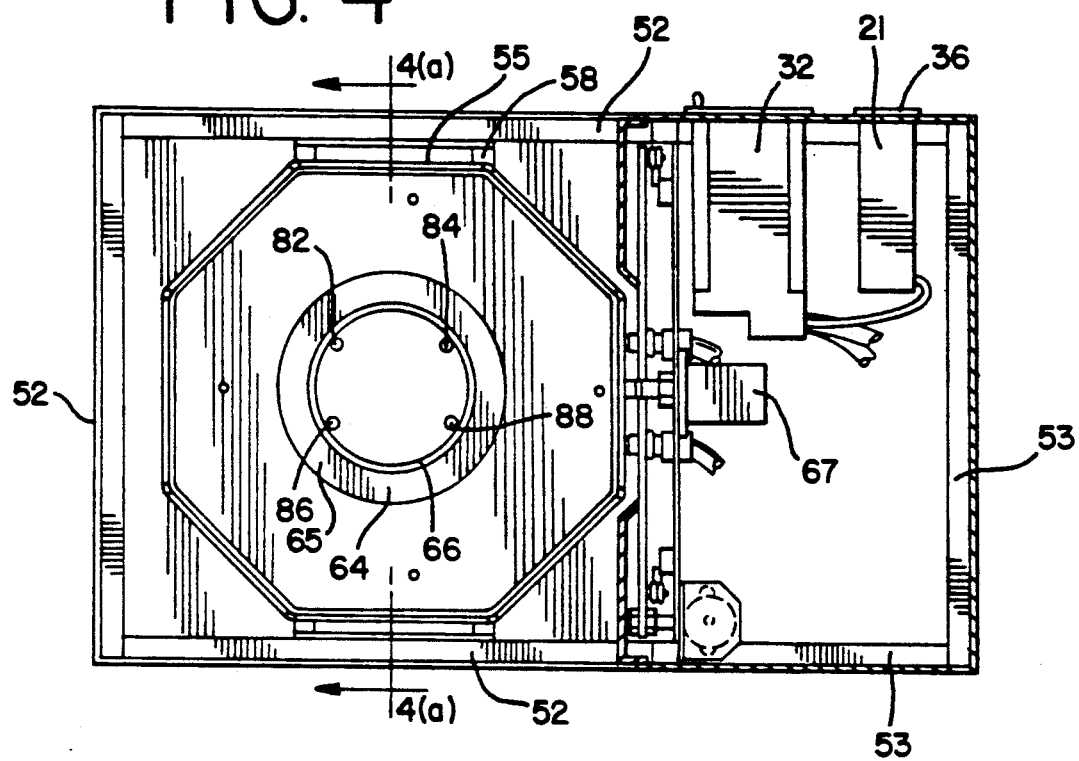
FIG. 4 is a bottom view of the furnace oven with the door removed, taken along the line 4—4 in FIG. 3.
Figure 5:
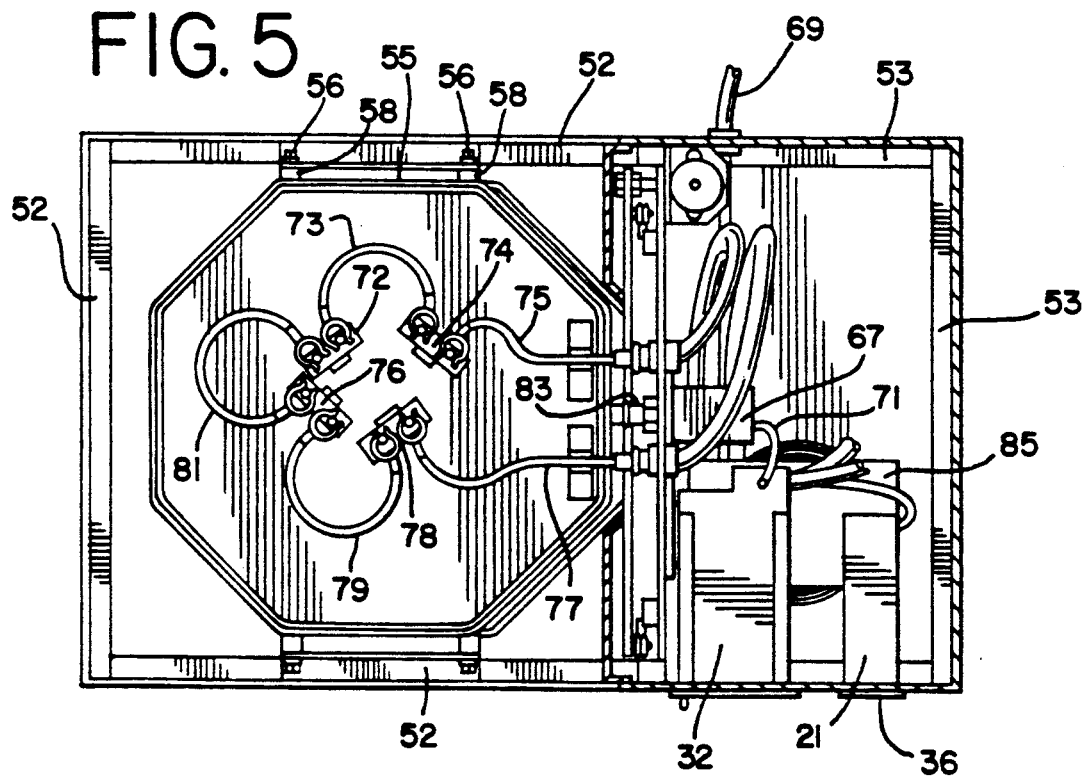
FIG. 5 is a top view of the furnace with the top protective panel removed, taken along the line 5—5 in FIG. 3.

All of the control instruments (temperature controls, display instruments, etc.) are conventional devices well known to persons skilled in the art. In the presently preferred embodiment, the temperature control and display instruments are available from Eurotherm, Inc. of Reston, Va. Referring to FIGS. 4 and 5, the display instrument 32 (which is electrically connected to the power switches 28 and 30) forms part of a Eurotherm SCR Power Controller 21, Model No. 832/20A/120V. The program/control instrument 36 is a Eurotherm Programmer/Controller, Model No. 808/4-20-MA/0808/D1/QP.

Referring again to FIGS. 1-3, the platform 40 includes an aluminum plate 42 mounted to lower horizontal members 41 of the stainless steel frame 25 with the aid of a plurality of fastener screws 44. The stainless steel frame 25 and the platform 40 support the control cabinet 20 and the furnace oven 50, as shown in FIGS. 1-3. Located below the lower horizontal members 41 of the stainless steel frame 25 and connected thereto, are a plurality of support legs 46 which serve to balance the high temperature research furnace 10, and to prevent the underlying bench top or other support surface being scratched or otherwise damaged by the steel frame 25.

Figure 4A:
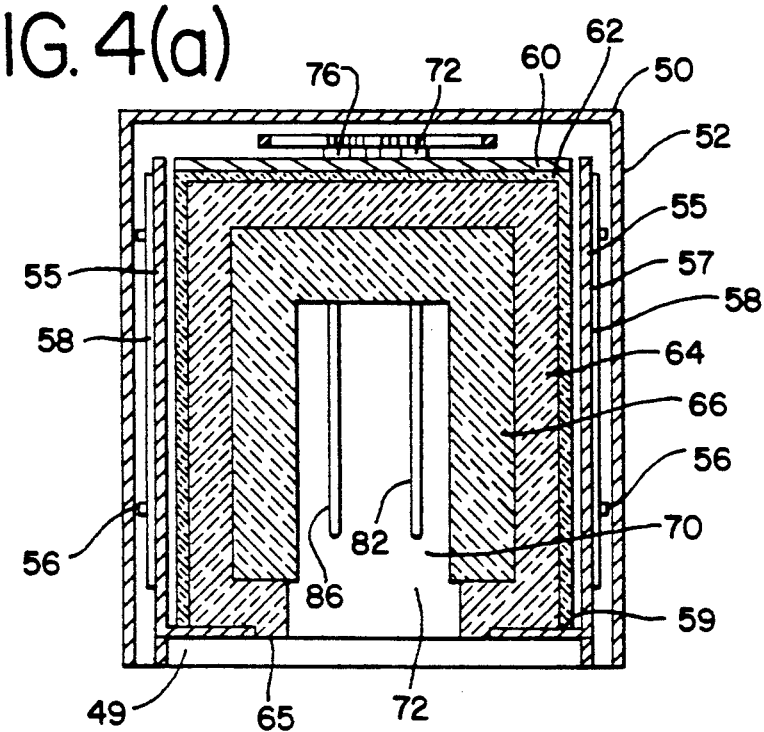
FIG. 4(a) is a sectional view of the inside of the furnace oven taken along the line 4(a)—4(a) in FIG. 4.

Referring now to FIGS. 1-7, the furnace oven 50 includes outer aluminum protective panels 52 on the top and sides which are mounted to the vertical members 51 (FIGS. 6-7) and upper horizontal members 53 of the stainless steel frame 25, using fastener screws 54. The protective panels 52 surround the oven housing 55 on the top and sides. The oven housing 55 includes a stainless steel panel having eight side sections 57 and a bottom section 59 as shown in FIGS. 4 and 4(a). Two of the steel side sections 57, on opposite sides of the oven housing 55, are each securely and permanently mounted to two vertically disposed stainless steel mounting brackets 58, each of which extends most of the vertical length of the oven housing 55 as shown in FIG. 4(a). The vertical mounting brackets 58 are in turn securely mounted to horizontal members of the stainless steel frame 25, as will be discussed more fully below.

Referring to FIG. 4(a), the furnace oven 50 further includes a one-quarter inch thick layer of felt insulation 62 which surrounds the oven chamber 70 on the top and sides, and which is adjacent to the stainless steel housing 55 on the sides. Preferably, the insulation layer 62 is spaced from the housing 55 on the sides, at a distance of up to one-half inch, to allow room for thermal expansion and contraction of the oven refractory layers discussed below. The presently preferred felt insulation material is Fiberfax Type 440J, available from the Carborundum Company, located in Barrington, Ill. Fiberfax 440J is made from a combination of ceramic fibers, inert fillers and fiberglass, and includes about 45.2% by weight silicon dioxide, about 33.1% by weight aluminum oxide, about 16.0% by weight calcium oxide, about 5.1% by weight magnesium oxide and about 0.6% by weight total of trace inorganic materials.

Located adjacent to the felt insulation layer 62, and closer to the oven chamber 70, is a one-inch thick layer 64 of Duraboard 2600 aluminum silicate refractory board, available from the Carborundum Company, Barrington, Ill. The Duraboard 2600 layer 64 includes about 56% by weight aluminum oxide, about 39% by weight silicon dioxide, and about 5% by weight of other inorganic materials. The refractory board layer 64 also surrounds the oven chamber 70 on the top and sides, and partially on the bottom.

Located adjacent to the refractory board layer 64, and also adjacent to and partially defining the oven chamber 70, is a 1.5-inch thick layer 66 of Sali refractory insulation material available from Zircar Products, Inc. of Florida, N.Y. The Sali refractory insulation layer 66 contains at least 96% by weight, and preferably more than 98% by weight aluminum oxide, with the remainder being mostly silicon dioxide. The Sali insulation layer 66 surrounds the oven chamber 70 on the top and sides.

The size of the oven chamber 70, and the thickness of the insulation layers 62, 64 and 66, may vary depending on the size of the furnace. In the embodiment shown, the oven chamber 70 is about six inches high, about six inches in diameter, and has an octahedral shape. The oven chamber 70 is surrounded on all sides by three layers of insulation 62, 64, and 66, except at the bottom opening 72 which receives the oven door. Therefore, the efficiency of the furnace 10, and the ability to reach high temperature in minimal time using minimal power, depends largely on the lifting mechanism and the ability to obtain a perfect, tight fit between the oven door 90 and the oven 50, so as to completely seal the opening 72, as will be discussed more fully below.

A layer 60 of hardboard refractory material lines the top of the oven 50, above and adjacent to the felt insulation layer 62, and extends between the side sections 57 of the stainless steel housing 55. The refractory sheet layer 60 is preferably a one-quarter inch thick of RS-100 refractory sheet, available from Zircar Products, Inc. of Florida, N.Y. The RS-100 layer 60 includes about 75% by weight aluminum oxide, about 16% by weight silicon dioxide, and about 9% by weight of other refractory materials.

Referring to FIGS. 4(a) and 5, the refractory sheet 60 supports four small blocks 72, 74, 76 and 78, each of which is constructed from refractory insulation material (preferably Sali), and each having a thickness of about one-half inch, a length of about two inches and a width of about one inch. Each of the refractory blocks houses the upper terminal portion of one of the hairpin heating elements 82, 84, 86 and 88 which extend from the respective refractory blocks through the refractory layers 60, 62, 64, and 66 and into the oven chamber 70 from above as shown in FIG. 4(a). As shown in FIG. 4(a), each of the hairpin heating elements extends about five inches down into the six-inch high oven chamber 70. As shown in FIG. 4, each of the hairpin heating elements 82, 84, 86 and 88 is located adjacent to the sides of the oven chamber 70.

The hairpin heating elements 82, 84, 86 and 88 can be standard molybdenum disilicide heating elements that are well known in the art. The use of the refractory blocks 72, 74, 76 and 78 to house the terminal portions of the heating elements constitutes an important feature with respect to the minimization of heat loss from the oven chamber 70. Without the refractory insulation blocks, the hairpin heating elements, and the openings in the insulation layers 60, 62, 64 and 66 through which the heating elements extend, would provide at least small conduits for the escape of heat from the oven chamber 70.

Referring to FIG. 5, electrical cables 73, 75, 77, 79 and 81 connect the heating elements 72, 74, 76 and 78 to a transformer 85 inside the control cabinet, and to the program/control instrument 36. An electrical insulation block 83 can also be provided which houses the terminal portion of a thermocouple 67. The thermocouple 67 is also connected to the programmer/controller 36 by the cable 71.

Referring to FIGS. 2 and 3, the door 90 of the furnace oven 50 includes an upper (platform) layer 92 of aluminum oxide-silica refractory insulation material, preferably Sali, which is preferably about one inch thick. The platform layer 92 has a diameter of approximately six inches, which should correspond almost exactly to the diameter of the opening in the refractory insulation material 66 in FIGS. 4 and 4(a). Below the platform layer 92 is an intermediate layer 94 of aluminum silicate refractory board, preferably Duraboard 2600, which is preferably one inch thick. The intermediate layer has a diameter which is slightly larger than the diameter of the platform layer, and which corresponds to the diameter of the opening in the refractory board layer 64 in FIGS. 4 and 4(a).

Below the refractory board layer 94 is a second refractory board layer 96, preferably of the same material, having a thickness of one inch, having a diameter much larger than the refractory board layer 94, and having an octahedral shape as shown in FIGS. 2 and 3. Referring to FIG. 4(a), the diameter of the refractory board layer 96 should be about eleven inches in order to permit the board layer 96 to interface with the lower lip 65 of the board layer 64, and with most of the bottom surface of the housing 55. Below the refractory board layer 96 and hidden from view is a one-quarter inch thick layer of felt insulation of similar diameter, preferably Fiberfax Type 440J as discussed above with respect to the layer 62.

The refractory board layer 96 and the underlying felt insulation material are adjacent to, and fit within, the stainless steel door housing 98 which abuts part of the lifting mechanism 100 discussed below. The stainless steel housing 98 is octahedral-shaped and is dimensioned to fit within the lower flange 49 of the stainless steel oven housing 55 shown in FIGS. 2 and 4(a), when the door 90 is raised. Referring now to FIGS. 2 and 4(a), when the door 90 is raised to the closed position, the platform layer 92 will be positioned laterally adjacent refractory insulation layer 66 of the same material of the oven; the intermediate refractory board layer 94 will be positioned laterally adjacent the refractory board layer 64 of the oven; the refractory board layer 96 will interface securely with the lower lip 65 of the refractory board layer 64 and with the corresponding lower surface of the stainless steel housing 55; and the stainless steel housing 98 of the door 90 will be positioned adjacent to the lower flange 49 of the stainless steel housing 55.

Before proceeding to a discussion of the lifting mechanism, a brief discussion of the stainless steel frame 25 is appropriate. Referring to FIGS. 1–7, the stainless steel frame 25 includes vertical members 51, upper horizontal members 53, lower horizontal members 41, and intermediate horizontal members 27. The vertical and horizontal members are arranged perpendicular to each other, and are securely joined together at the ends, to create a stable, secure structure. While the stainless steel frame can be constructed in a variety of ways familiar to persons skilled in the art, it is very important that the furnace oven 50 be maintained in a secure position, free of movement, play or tilt. In order to allow the lifting mechanism 100 to open and close the door securely in the same position relative to the oven 50 every time, so as to minimize heat losses, the oven 50 must not be allowed to move or tilt relative to the door 90.

Referring to FIGS. 6 and 7, the outer housing 55 of the oven 50 is securely mounted on opposite sides to four vertical support brackets 58 which extend over most of the vertical length of the housing 55. The housing 55 can be mounted to the support brackets 58 using the screws 56 as shown, or using any suitable fastening means. The vertical support brackets 58 are, in turn, mounted near their lower ends to the horizontal frame members 27. Each horizontal frame member 27 is mounted at an end to a respective one of the vertical frame members 51 which extends from the lower horizontal frame member 41 to the upper horizontal frame member 53. In order to prevent tilting of the oven 50, braces 29 are provided which intersect each respective vertical frame member 51 and horizontal frame member 27 at 45-degree angles, and which are securely fastened to the frame members 51 and 27.

Figure 10:
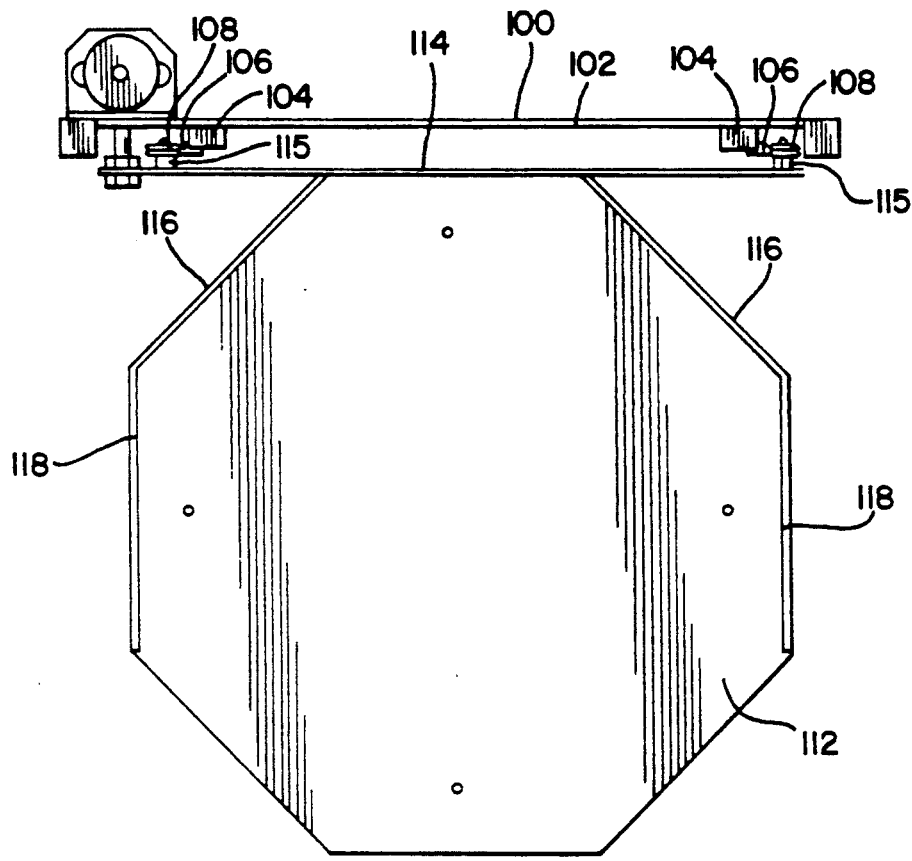
FIG. 10 is a top plan view of the lifting mechanism of FIG. 8.

Referring now to FIGS. 8-10, the lifting mechanism 100 includes, first, a vertically disposed, one-eighth inch thick aluminum support panel 102, which extends the length of the vertical frame members 51 and which is securely fastened thereto. A pair of vertically-disposed rectangular guide members 104, each having at least one V-track 106 along a longitudinal edge thereof, are firmly mounted to the front of the support panel 102 using a large number of fastener screws 103. The guide members 104 are positioned near the lateral edges of the support panel 102, with each guide member 104 extending the vertical length of the support panel 102.

As shown in FIGS. 9 and 10, each V-track 106 engages two V-wheels 108, with each of the four V-wheels 108 being rotatably mounted to a carriage 110. The carriage 110 is constructed from one-eighth inch thick cantilevered aluminum and includes a horizontally disposed carriage platform 112, a vertically disposed back frame 114, two platform braces 116 and two side walls 118. The V-wheels 108 are rotatably mounted to the back surface of the carriage back frame 114, using mounting shafts 115 which facilitate rotation in both directions parallel to the back surface of the back frame 114. The use of four V-wheels 108 engaging two V-tracks 106 in the manner shown, reduces the amount of "play" in the lifting carriage 110 to an absolute minimum.

The carriage platform 112 is perpendicular to the back frame 114 and is reinforced by the platform braces 116 which are triangular-shaped, which are disposed perpendicular to the carriage platform 112, and which have edges securely fastened to two edges of the back frame 114 and two edges of the carriage platform 112. Referring to FIG. 10, the platform braces are disposed perpendicular to the octahedral-shaped platform 112 along two of its edges. The platform side walls 118 are also disposed perpendicular to the carriage platform 112 along two opposite edges which are adjacent to the two edges occupied by the platform braces 116. The back frame 114, platform braces 116, platform walls 118 and carriage platform 112 define a partial enclosure which is sized so as to receive and firmly engage the oven door 90 as shown in FIGS. 2 and 3. Once the oven door 90 is firmly mounted to the platform 112 as shown in FIGS. 2 and 3, the oven door is prevented from experiencing free-play due to the configuration of the lifting mechanism as described above.

Referring to FIGS. 8 and 9, the back frame 114 of the carriage 110 is connected via bolt 117 to a connector rod 120 which extends through a tall, narrow slot 105 in the aluminum support panel 102, and connects to a lower end of a long, vertically disposed threaded rod 122 located behind the support panel 100. The threaded rod 122 engages, near its upper end, to a reversible motor 124 which is securely mounted higher up on the back side of the support panel 102. When the up-down switch 21 shown in FIG. 1 is in the "up" position, the motor 124, engaged to the threaded rod 122, turns so as to pull the threaded rod 122 up, causing the connector rod 120 to move upward in the slot 105, in turn causing the carriage 110 to be raised until the oven door 90 is in a closed position as in FIG. 1. When the up down switch 21 is in the "down" position, the reversible motor 124 turns in the opposite direction, causing the lowering of the threaded rod 122, the connector rod 120 and the carriage 110 until the oven door 90 is in the fully open position as shown in FIG. 3. The up-down switch 21 may, at any time, be moved to a "neutral" position causing the motor 124 to stop, and causing the carriage 110 and the oven door 90 to remain in an intermediate position as shown in FIG. 2.

The reversible motor 124 which is presently employed is a Hurst 4013-001 Linear Actuator, available from Minarik Company in Glendale, Calif. Other suitable motors may also be employed including a Ball Drive Activator Model No. 85151/85152 which, instead of moving the threaded rod 120, would activate a movable nut engaged to the lower end of a threaded rod 122. The nut, which would be mounted to the connector rod 120 behind the panel 100, would climb the threaded rod 122 (which would be stationary as the movable nut turns), causing the carriage 110 to be lifted relative to the threaded rod 122, and would retract when the direction of the motor is reversed. Other equivalent lifting means may be employed, or the carriage may be raised and lowered manually.

The heating elements 82, 84, 86 and 88 are presently powered using a 1.6 KVA or 2.0 KVA transformer 85 (FIG. 5), which is connected to a standard 115-volt wall outlet. A single electrical power cord 69 connected to the standard 115-volt wall outlet powers the transformer 85, and branches off to separately power the reversible motor 124 and the control cabinet instruments. The power cord 69 enters the control cabinet and branches off to separately power the reversible motor 124 and the programmer/controller 36. The programmer/controller 36 is employed to pulse power to the transformer 85, which is connected in series with the heating elements 82, 84, 86 and 88. In the preferred embodiment, the programmer/controller 36 provides a train of 115-volt pulses to the transformer 85. The 115-volt power cord 69 also couples to the three-way lift motor switch 21 coupled to the reversible motor 124 in a manner generally known in the art. For larger furnace sizes, more powerful transformers may be employed.

The combination of advantageous features including the novel lifting mechanism, the design and fitting of the door and the furnace oven, and the use of insulation blocks on top of the furnace oven to house the terminal portions of the heating elements, operate together to minimize the escape of heat from inside the furnace. This minimal heat escape, in turn, allows the furnace to reach temperatures of at least 1700° C. within a minimal amount of time, and to maintain these temperatures, using only the power that can be drawn from a standard 115-volt wall outlet.

Figure 11:
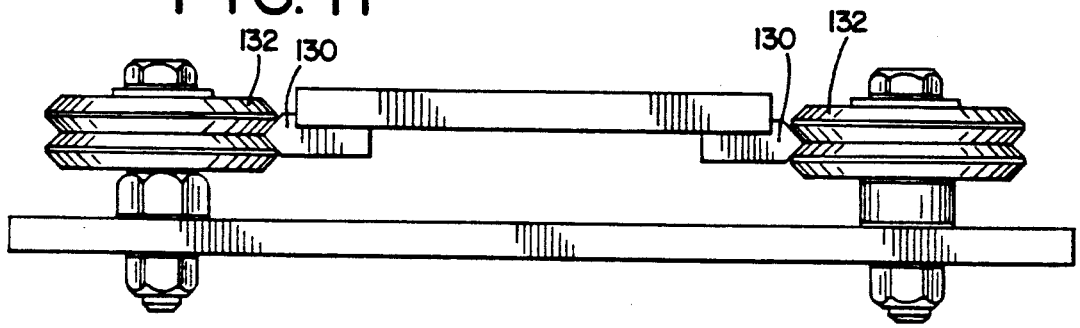
FIGS. 11, 12, 13 and 14 show alternative embodiments for the relative mounting of the V-guide wheels and tracks.
Figure 12:
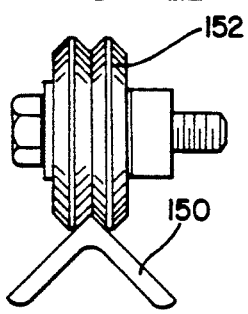
Figure 13:
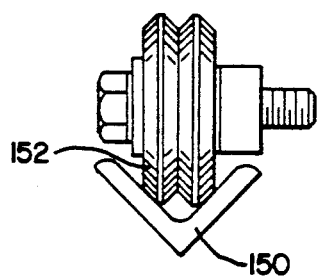
Figure 14:
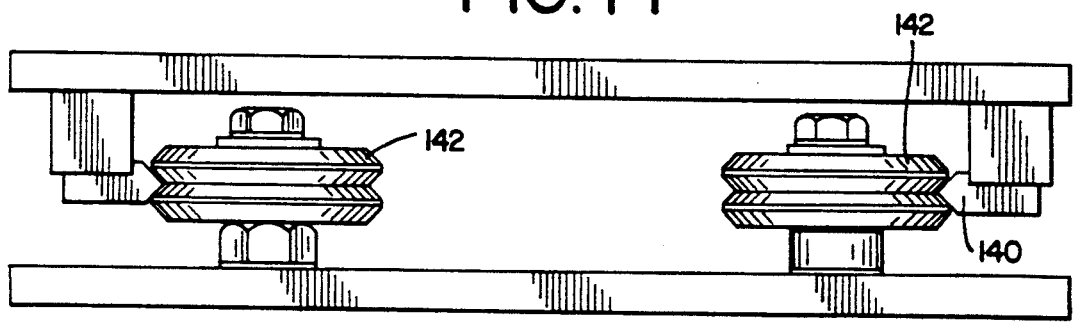

FIGS. 11-14 illustrate alternative embodiments of the lifting mechanism 100 which employ different relationships between the V-wheels and the V-tracks. For instance, the V-tracks 130 and V-wheels 132 can be mounted so that the V-tracks are disposed between the V-wheels, and engaged thereto, as shown in FIG. 11. Alternatively, the V-tracks 140 and V-wheels 142 can be mounted as in FIG. 14, so that the V-wheels are disposed between the V-tracks and engaged thereto. Alternatively, the V-tracks 152 and V-wheels 150 can be mounted to that the V-wheels engage either side of hollow V-tracks as shown in FIGS. 12 and 13. V-tracks and V-wheels which can be arranged in the foregoing configurations, and which are suitable for use with the invention, are available from the Bishop-Wisecarver Corporation, Pittsburg, Calif. During operation of the research furnace 10 of the invention, the V-guides and V-wheels are protected from dust and concealed from view, by the cover panels 101 as shown in FIGS. 1-3.

EXAMPLE 1

A high temperature research furnace as described above was operated using a constant current of 45 amperes. The oven was powered using a 1.6 KVA transformer, supplied by a 115-volt wall outlet socket. The temperature of the oven was recorded at several time increments. The following table shows the furnace temperature as a function of time.

| Time (Minutes) | Temperature (°C.) | Current (Amps) | Voltage | KVA |
| --- | --- | --- | --- | --- |
| 0 | 17 | 45 | 3.0 | .135 |
| 1 | 22 | 45 | 3.8 | .171 |
| 2 | 56 | 45 | 6.0 | .270 |
| 3 | 100 | 45 | 7.0 | .315 |
| 4 | 144 | 45 | 7.8 | .351 |
| 5 | 180 | 45 | 8.0 | .360 |
| 7 | 246 | 45 | 8.3 | .374 |
| 9 | 302 | 45 | 9.0 | .405 |
| 12 | 385 | 45 | 9.9 | .446 |
| 30 | 769 | 45 | 12 | .540 |
| 45 | 1046 | 45 | 16 | .720 |
| 60 | 1270 | 45 | 19 | .855 |
| 75 | 1460 | 45 | 22 | .990 |
| 90 | 1600 | 45 | 24 | 1.08 |
| 105 | 1700 | 45 | 25 | 1.13 |
| 115 | 1700 | 45 | 23 | 1.04 |

From the foregoing, it was concluded that the high temperature research furnace of the invention can attain the standard maximum temperature of 1700° C. in less than two hours, using only the power that is available from a 1.6 KVA transformer driven by a 115-volt wall outlet.

While the embodiments of the invention disclosed herein are presently considered to be preferred, various changes and modifications can be made without departing from the spirit and scope of the invention. The scope of the invention is indicated in the appended claims, and all changes that fall within the meaning and range of equivalency of the claims are intended to be embraced therein.

We claim:

1. A high temperature furnace for use in laboratories, comprising:

a control cabinet;

a support platform underneath the control cabinet, with a portion of the platform extending beyond the control cabinet;

an elevated furnace oven adjacent to the control cabinet positioned above the portion of the platform extending beyond the control cabinet, the elevated furnace oven having a top, sides, bottom, a chamber, and a door which opens from the bottom of the oven;

a support frame for securing the control panel, support platform and furnace oven in their respective positions relative to each other; and a lifting mechanism for elevating the oven door to a closed position at the bottom of the oven, and for lowering the oven door to an open position below the bottom of the oven and above the support platform;

the lifting mechanism comprising a vertically disposed support panel securely fastened to the support frame, the support panel including two vertically disposed rectangular guide members mounted to a front surface of the support panel, each of the guide members having a V-track along a longitudinal edge thereof;

the lifting mechanism further comprising a carriage for carrying the oven door, the carriage having at least two V-wheels rotatably mounted thereto, with each of the two V-wheels engaging the V-track on one of the guide members;

the lifting mechanism further comprising means for raising and lowering the carriage.

2. The high temperature furnace of claim 1, wherein the lifting mechanism further comprises a vertically disposed longitudinal slot in the support panel; a connector rod fastened at one end to the carriage and extending through the slot; and a vertically disposed threaded rod located behind the support panel and engaged at its lower end to a second end of the connector rod; the threaded rod being engaged at its upper end to a reversible motor such that when the motor turns, the carriage is raised and lowered; the motor being mounted to a back surface of the support panel.

3. The high temperature furnace of claim 1, wherein the carriage comprises a back frame, a carriage platform perpendicular to the back frame, two platform braces having edges connected to two edges of the back frame and two edges of the carriage platform, and two platform side walls perpendicular to the carriage platform along two opposite edges of the carriage platform.

4. The high temperature furnace of claim 3, wherein the carriage platform is octahedral-shaped.

5. The high temperature furnace of claim 1, wherein the carriage has four V-wheels rotatably mounted thereto, with two of the V-wheels engaging the V-track on each of the guide members.

6. The high temperature furnace of claim 1, wherein the furnace oven comprises an oven chamber surrounded on the top and sides, and partially on the bottom, by a first inner layer of an aluminum oxide-silica refractory insulation material, a second layer of aluminum silicate refractory board, and a third layer of a ceramic felt insulation material.

7. The high temperature furnace of claim 6, wherein the oven chamber has a height of about six inches and a diameter of about six inches, the first inner layer has a thickness of about one and one-half inches, the second layer has a thickness of about one inch, and the third layer has a thickness of about one-quarter of an inch.

8. The high temperature furnace of claim 6, wherein the furnace oven further comprises an outer stainless steel housing.

9. The high temperature furnace of claim 6, wherein the furnace oven further comprises a fourth top layer of hardboard refractory material adjacent the third layer.

10. The high temperature furnace of claim 9, further comprising a plurality of hairpin heating elements extending through the four layers and into the oven chamber from the top, each of the heating elements having a terminal portion above the fourth top layer which is housed in a refractory block, each of the refractory blocks being mounted securely to the top layer.

11. The high temperature furnace of claim 1, wherein the oven door comprises an upper platform layer of an aluminum oxide-silica refractory insulation material, a second layer of aluminum silicate refractory board, a third layer of aluminum silicate refractory board, and a fourth layer of a ceramic felt insulation material.

12. The high temperature furnace of claim 11, wherein the top platform layer has a thickness of about one inch, each of the second and third layers have a thickness of about one inch, and the fourth layer has a thickness of about one-quarter of an inch.

13. The high temperature furnace of claim 11, wherein the top platform layer and oven chamber have diameters which are approximately equal, the second layer has a diameter slightly larger than the diameter of the top platform layer, and the third and fourth layers each have diameters larger than the diameter of the second layer.

14. The high temperature furnace of claim 11, wherein the oven door further comprises a stainless steel housing dimensioned such that the third and fourth layers are adjacent to and fit within the housing.

15. A high temperature research furnace for use in laboratories, comprising:
a control cabinet;
a support platform underneath the control cabinet;
an elevated oven positioned laterally of the control cabinet and at an elevation higher than that of the support platform, the furnace oven housing a top, sides, bottom, a chamber, and a door which opens from the bottom of the oven; and
a lifting mechanism which elevates the oven door to a closed position at the bottom of the oven, and lowers the oven door to an open position below the bottom of the oven;
the lifting mechanism comprising a vertically disposed support panel securely fastened to the support frame, a carriage for the oven door movable vertically at a fixed horizontal distance from the support panel, and means for raising and lowering the carriage;
the vertically disposed support panel comprising two vertically disposed guide members mounted to a front surface of the support panel, each of the guide members having a vertically disposed V-track along an edge thereof;
the carriage comprising at least two V-wheels rotatably mounted thereto, with one of the two V-wheels engaging the V-track on each of the guide members.

16. The high temperature research furnace of claim 15, wherein the lifting mechanism further comprises a vertically disposed longitudinal slot in the support panel; a connector rod fastened at one end to the carriage and extending through the slot; and a vertically disposed threaded rod located behind the support panel and engaged at its lower end to a second end of the connector rod; the threaded rod being engaged at its upper end to a reversible motor such that, when the motor turns, the carriage rod is raised and lowered; the motor being mounted to a back surface of the support panel above the longitudinal slot.

17. The high temperature research furnace of claim 15, wherein the carriage comprises a vertically disposed back frame, a horizontally disposed carriage platform connected to the back frame, two triangular platform braces fastened to the back frame and carriage platform, and two sidewalls disposed perpendicular to the carriage platform along two opposite edges thereof; the back frame, platform braces, platform walls and carriage platform defining a partial enclosure which is sized so as to receive and firmly engage the oven door.

18. The high temperature research furnace of claim 15, wherein the carriage has four V-wheels rotatably mounted thereto, with two of the wheels engaging the V-track on each of the guide members.

19. A lifting mechanism for a high-temperature laboratory furnace, comprising:
a vertically disposed support panel having a vertically disposed longitudinal slot therein;
two vertically-disposed rectangular guide, members mounted to a front surface of the support panel, each of the guide members having a V-track along a longitudinal edge thereof;
a carriage for carrying an oven door, comprising an upright back frame, a horizontal carriage platform, one or more side walls, and four V-wheels rotatably mounted to the back frame such that two of the V-wheels engage each of the two V-tracks;
a reversible motor mounted to a back surface of the support panel above the longitudinal slot;
a vertically-disposed threaded rod engaging the reversible motor and extending downward therefrom; and
a connector rod passing through the longitudinal slot, having a first end fastened to the carriage and a second end fastened to the vertically disposed threaded rod;
such that when the reversible motor turns in one direction the carriage is raised, and when the reversible motor turns in an opposite direction the carriage is lowered.

* * * * *

UNITED STATES PATENT AND TRADEMARK OFFICE
CERTIFICATE OF CORRECTION

PATENT NO. : 5,313,048
DATED : May 17, 1994
INVENTOR(S) : Morris Berg et al.

It is certified that error appears in the above-indentified patent and that said Letters Patent is hereby corrected as shown below:

On the Title Page

Item [56] "OTHER PUBLICATIONS" delete "Data" and substitute --Date--.

Item [57], line 2 of the "ABSTRACT", delete the second occurrence of "a".

Signed and Sealed this

Sixth Day of June, 1995

Attest:

BRUCE LEHMAN

*Attesting Officer*    *Commissioner of Patents and Trademarks*